United States Patent [19]

Clark

[11] Patent Number: 5,141,718
[45] Date of Patent: Aug. 25, 1992

[54] TEST PLATE APPARATUS

[75] Inventor: Phillip Clark, Stoneham, Mass.

[73] Assignee: Millipore Corporation, Bedford, Mass.

[21] Appl. No.: 605,611

[22] Filed: Oct. 30, 1990

[51] Int. Cl.$^5$ .......................... B01L 3/00; C12M 3/04
[52] U.S. Cl. ................................. 422/99; 422/101; 422/102; 435/285; 435/300; 435/311
[58] Field of Search .............. 435/285, 286, 300, 301, 435/311, 293, 297; 422/99, 101, 102; 210/238

[56] References Cited

U.S. PATENT DOCUMENTS

| | | | |
|---|---|---|---|
| 3,649,464 | 3/1972 | Freeman | 422/99 |
| 4,154,795 | 5/1979 | Thorne | 435/300 |
| 4,761,378 | 8/1988 | Godsey | 435/300 |
| 5,009,780 | 4/1991 | Sarrasin | 210/238 |

FOREIGN PATENT DOCUMENTS 0408940 1/1991 European Pat. Off. ............ 435/311

Primary Examiner—James C. Housel
Assistant Examiner—William Chan
Attorney, Agent, or Firm—Paul J. Cook; Andrew T. Karnakis

[57] ABSTRACT

A test plate apparatus is provided having at least one set of wells comprising two essentially parallel rows of wells and a central area between the wells. Each well has a first volume for housing means for effecting a fluid interaction process such as for cell growth and a second volume which permits addition or removal of liquid from the wells without disturbing the fluid interaction process.

9 Claims, 5 Drawing Sheets

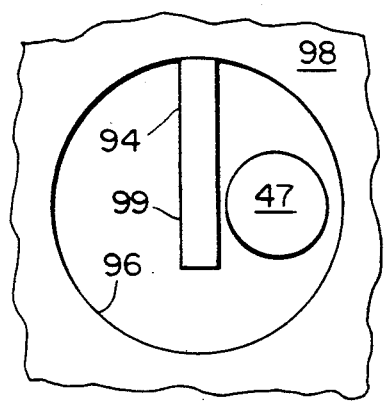
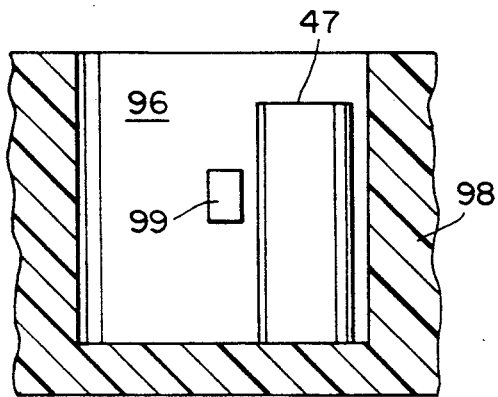
Fig. 12
Fig. 13
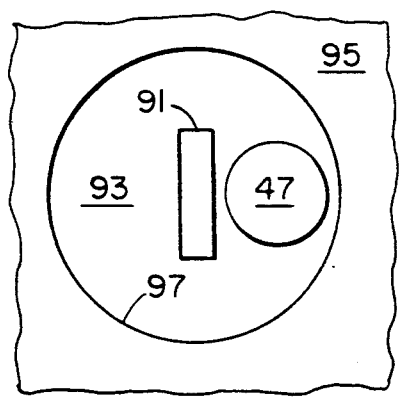
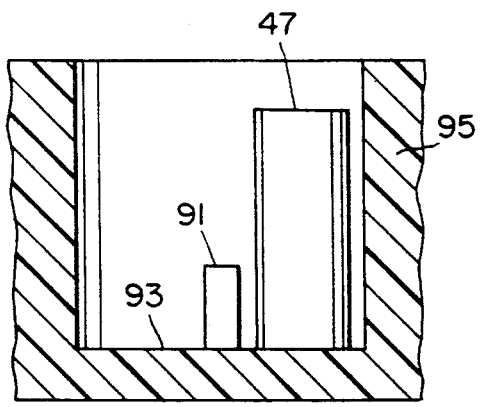
Fig. 14
Fig. 15

TEST PLATE APPARATUS

BACKGROUND OF THE INVENTION

This invention relates to a test plate apparatus suitable for promoting fluid interactions such as by growing cells in a nutrient liquid within a multiplicity of wells. More particularly, this invention relates to such a test plate apparatus which permits adding or removing liquid from wells in the test plate without disturbing the material such as cells within the wells.

At the present time, multi-well test plates are provided wherein the wells have a circular shape and size which permits the introduction therein of a tubular member having a membrane upon which cell attachment, growth and differentiation occurs. The microporous member allows free diffusion of ions and macromolecules between cells and their apical and basolateral surfaces through a liquid medium which surrounds the tubular member and which permeates the membrane. The test plates containing the wells are rectangular and having a standard size of about 3.25 inches by 5 inches in order to accommodate standard analytical apparatus. Since the plate size is define and since it is desired to avoid corners in the wells to avoid liquid stagnation areas, the wells are circular. In addition, the clearance between the interior well wall and the outside wall of the tubular member insert is minimized. The member insert is generally as large as possible to maximize the cell growth-area which leads to a lower error in the data gathering. However, a balance exists in that the basal and apical fluid volumes should be as close to for easy pipeting, to minimize fluid pressure between inner and outer wells and as large as possible to reduce the frequency of pipetting. This space requirement renders it difficult to insert pipetting means into the well to remove or add liquid while the tubular member is positioned within the well. The periodic removal of liquid to remove cell waste and additions of liquid to provide cell nutrients is required to maintain cell viability. In addition, cell based assay protocols require fluid manipulation. In addition, automatically controlled pipetting means cannot be used since the tubular member position is random and the probability that the pipetting means would damage the cells and pierce the membrane is high.

Thus, it is presently necessary to pipette manually in order to avoid cell damage by the pipetting apparatus. This procedure is time-consuming, since it generally requires individual well treatment and is undesirable, since it may cause cell damage. Accordingly, it would be desirable to provide a test plate arrangement which permits removing or adding liquid from or to wells in the cell plate which permits the use of standard automatic pipetting means.

SUMMARY OF THE INVENTION

The present invention provides a test plate having wells shaped to accommodate a device, including a membrane which permits cell growth on the membrane and to isolate the device within a first volume of the well so that a second volume of the well remains open. The second volume of the well communicates with the first volume of the well and is sufficiently large to provide an access area to accommodate a pipette for delivering or removing liquid to or from the well without disturbing cells in the device within a nondisturbed area of the well. The wells are formed in rows on the test plate. Means are provided for maintaining the cell-retaining device within the first volume comprising the nondisturbed area of the wells so that the cells are not disturbed when liquid is added to or removed from the second volume comprising the access are of the wells.

BRIEF DESCRIPTION OF THE DRAWINGS

FIG. 12 is a top view of well having an extension from the well wall to restrict movement of a tubular member.

FIG. 13 is a side view of the well of FIG. 12.

FIG. 14 is a top view of a well having an extension from the well floor to restrict movement of a tubular member.

FIG. 15 is a side view of the well of FIG. 14.

DESCRIPTION OF SPECIFIC EMBODIMENTS

While the present invention is described in terms o effecting cell growth, it is to be understood that the present invention is applicable to manipulations involving an access area for introducing or removing fluid and a nondisturbed area wherein the desired processing is effected, for example cell growth, dialysis or diffusional separation.

This invention is based upon the concept of providing a test plate containing a plurality of wells shaped to accommodate means for retaining cells and for allowing cell growth while permitting automatically controlled manipulation procedures to promote cell growth without adversely affecting cell growth. In addition, means are provided to maintain the means for retaining cells within a first volume of the well while permitting access to a second volume of the well with means for promoting cell growth without disturbing the growing cells. The means for positioning the cell retaining means can comprise the well shape or can comprise complementary ridge and slot means forming part of the cell retaining means and the plate.

Figure 1:
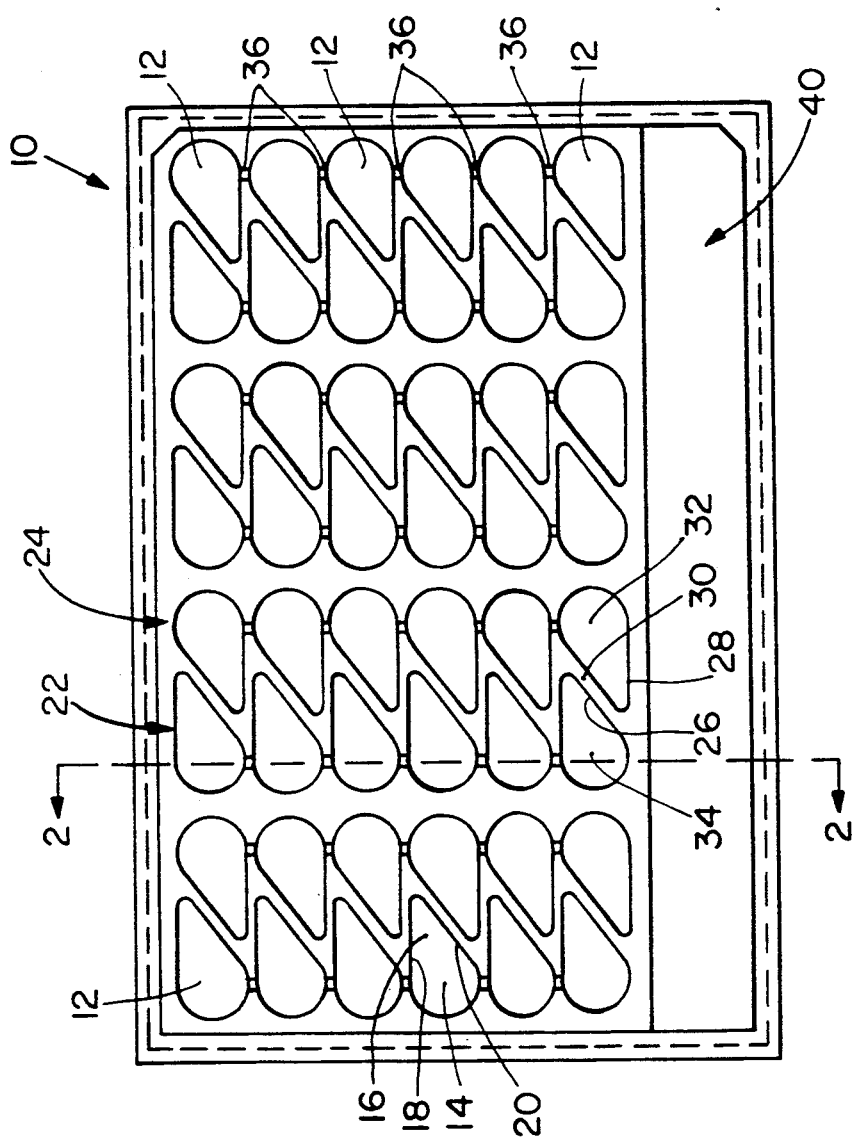
FIG. 1 is a top view of a test plate of the invention.
Figure 2:
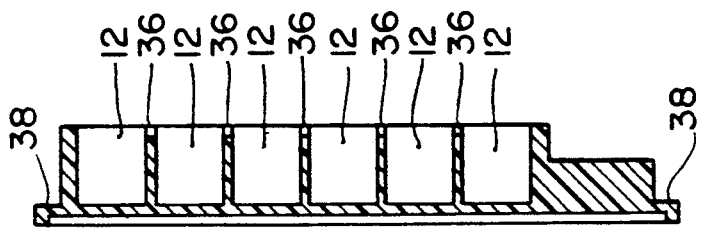
FIG. 2 is a cross-sectional view of the plate of FIG. 1 taken along line 2—2.

Referring to FIG. 1 plate 10 is shown for illustration purposes which include a plurality of wells 12. The wells have a tear-drop shape comprising a circular portion cross section 14 and a triangular section 16 formed from the two converging legs 18 and 20. The tear-drop shaped wells 12 comprise a preferred form of the wells of this invention since the well is free of sharp corners where liquid can stagnate.

A set of two rows of wells such as the row of six wells 22 and the row of six wells 24 are positioned so that the triangular sections such as sections 26 and 28 extend into a central portion 30 positioned between the circular portion cross section 32 and 34 of wells 12. Slots 36 are provided in the solid portions of the plate 10 between wells 12 for reasons which will be explained below. A shelf 38 can be provided in order to support a cover over the wells 12 if desired. Furthermore, an additional number of wells can be provided in area 40 if desired.

Figure 4:
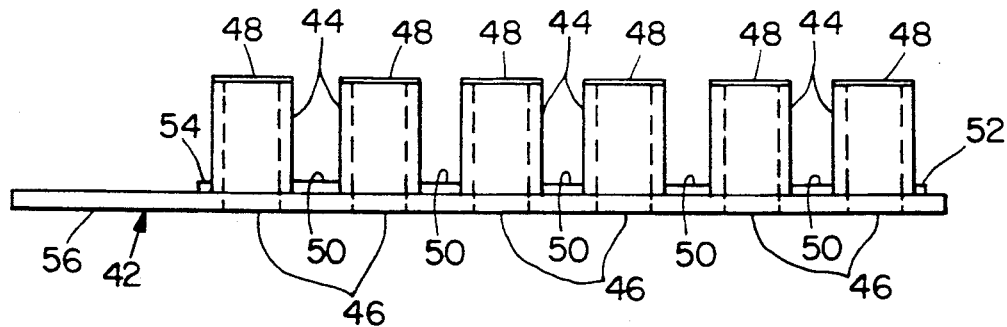
FIG. 4 is a side view of the strip of 3.
Figure 3:
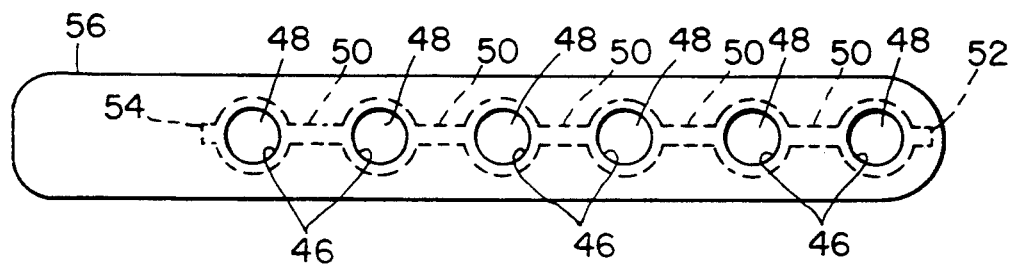
FIG. 3 is a top view of a strip of a plurality of cell retention devices useful in the present invention.
Figure 5:
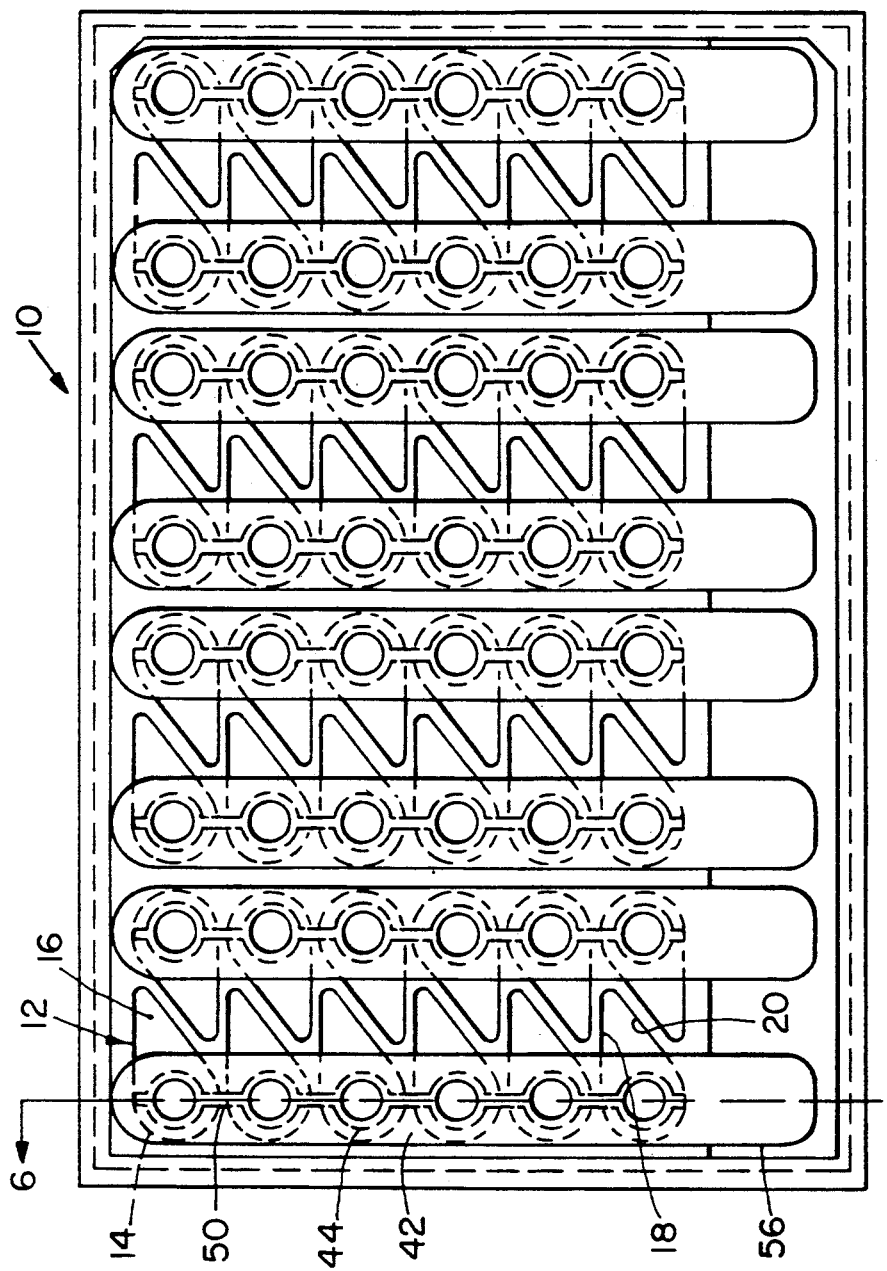
FIG. 5 is a top view of the test plate of FIG. 1 with the strip of FIG. 3 in place.
Figure 6:
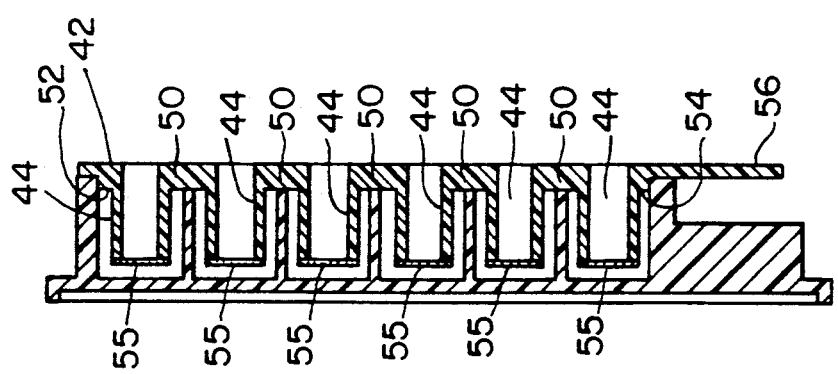
FIG. 6 is a cross-sectional view of the device of FIG. 5 taken along line 6—6.

FIGS. 3 and 4 show a unitary strip 42, including a plurality of tubular members 44 having open ends 46 and a bottom which is rendered closed by having a membrane 48 sealed thereto. The strip 42 includes a segmented ridge 50 which fits into slots 36 when the strip 42 is positioned within a row of wells 12 in plate 10 (see FIGS. 1 and 5). The strip 42 is provided with end ridges 52 and 54 which contact an inner surface of a well 12 at the ends of each row of wells. The slots 36, ridge 40 and end ridges 52 and 54 serve to maintain the tubular members in place within the circular portion 14 of wells 12 (see FIG. 5). As shown in FIG. 5, the strip 42 is positioned so that the tubular member 44 having open end 46 fits within the circular portion 14 of wells 12. Even if the ridge 50 becomes dislodged from the slots 36, the tubular members 44 cannot enter the entire triangular portion 16 of well 12 because the width of the triangular portion 16 becomes less than the outer diameter of the tubular member 44. Thus, at least a portion of the triangular section remains open and free of the tubular member 44 so that pipetting be effected within the triangular section 12 without disturbing cells on membrane 48 within the circular portion 14. The strip 42 can be provided with a handle 56 to promote ease of positioning the tubular members 44. Alternatively, additional wells 12 can be provided in plate 10 in the area occupied by the handles 56.

Figure 7:
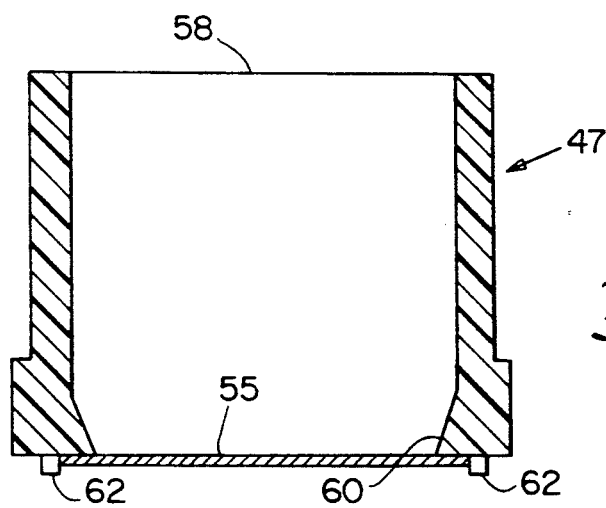
FIG. 7 is a cross-sectional view of a single cell retention device useful in the present invention.
Figure 8:
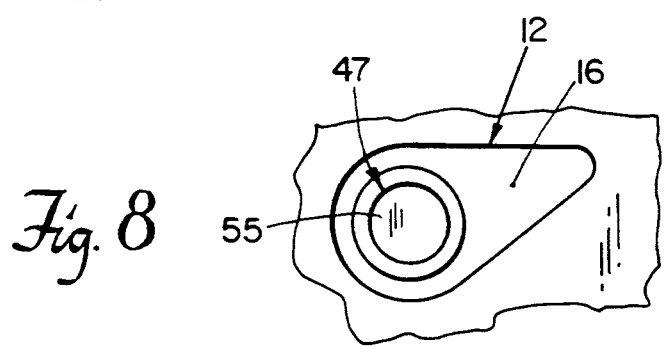
FIG. 8 is a partial top view of the cell retention device of FIG. 7 in place within a well of the plate of FIG. 1.

Referring to FIGS. 7 and 8, an individual tubular member 47 is shown having an open end 58 and a closed end 60. The closed end 60 comprise a membrane 55 useful for growing cells such as is disclosed in U.S. Pat. No. 4,917,793, which is incorporated herein by reference. The membrane 55 is sealed over the entire periphery of end 60. It is preferred that the tubular member 44 be transparent in order to enhance viewing of cell growth within membrane 55. In use, the closed end 60 is immersed into an aqueous growth medium in well 12 and then viable cells are introduced onto membrane 55. Spaced apart protrusions 62 are provided to space membrane 55 apart from the bottom surface of well 12 so that both the top and bottom surfaces of the cells contact the growth medium.

The growth medium outside of the tubular members 44 is periodically replaced with fresh growth medium by means of a pipette, which extends into triangular section 16 of well 12 without disturbing the cells or membrane 55 within tubular member 44. The media inside the well 46 need only be changed after the cells have attached and formed a monolayer by pipetting from inside the well 44.

Figures 9, 10, 10A:
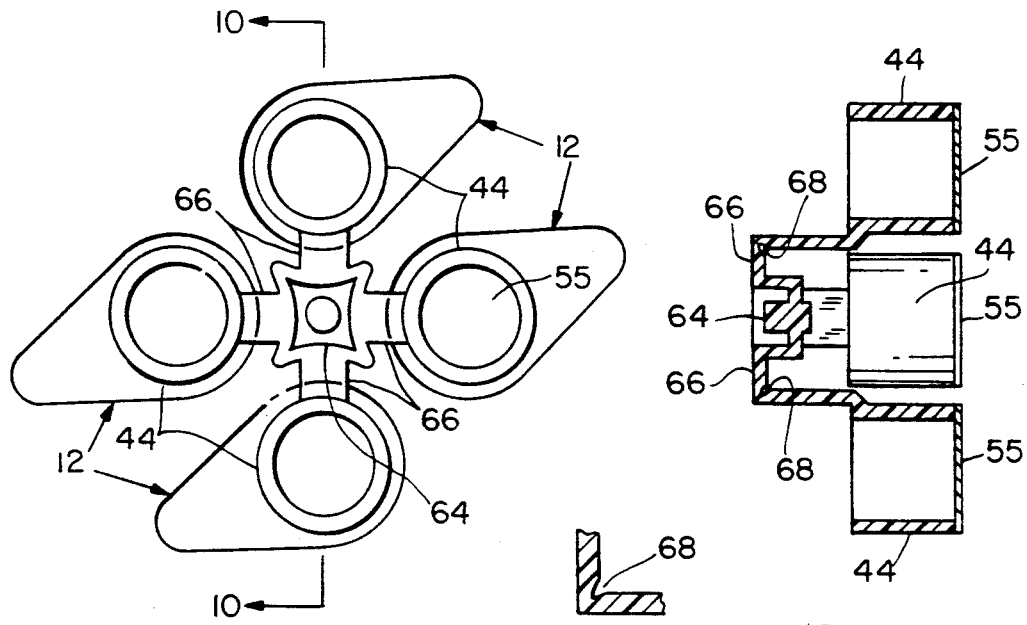
FIG. 9 is a top view of cluster of wells useful in the present invention.
FIG. 10 is a cross-sectional view of the cluster of FIG. 9 taken along line 10—10 without showing the wells.
FIG. 10a is an expanded view showing the notch (68) which allows for easy breakage of the tubular member (44).

An alternative means for including a p or tubular member on a unitary device is shown in FIGS. 9 and 10. The tubular member 44 and sealed membrane 55 are arranged as a cluster of four on a common central support 64 and arms 66. The tubular member 44 fit into four adjacently-positioned wells 12. The arms 66 can be provided with a notch 68 to permit easy breakage of the tubular member 44 from the arm 66. The means shown in FIGS. 9 and 10 can be expanded to include additional wells, e.g. 8, 12, 16, etc., if desired.

Figure 11:
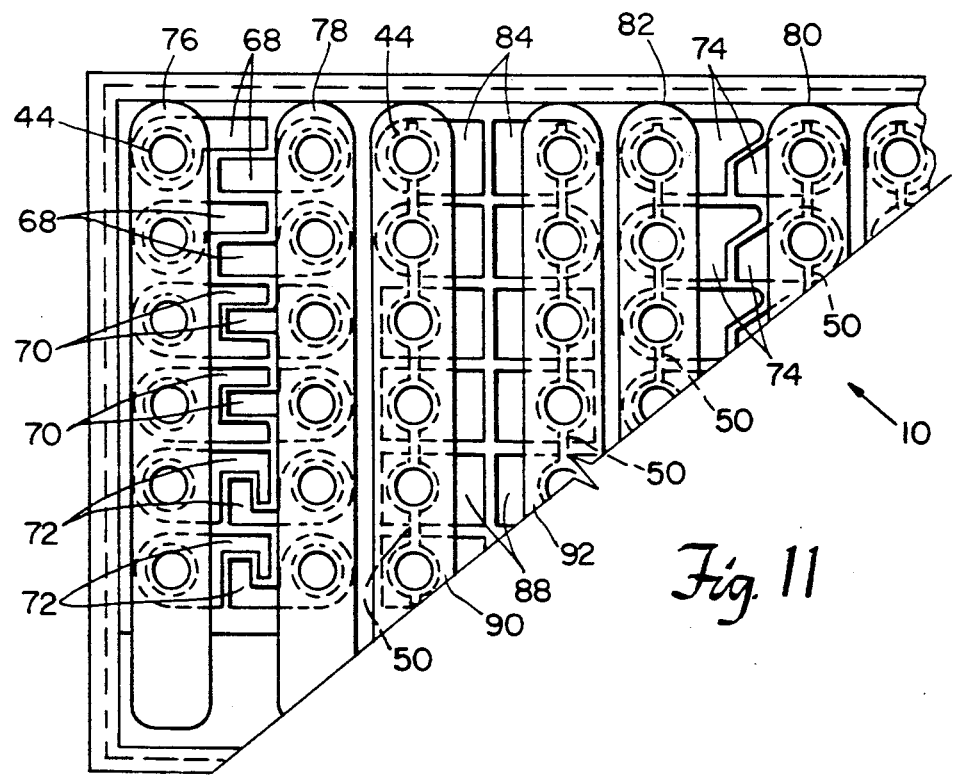
FIG. 11 is a top view of various well designs useful in the present invention while accommodating the strip of FIG. 3.

Referring to FIG. 11, a plurality of differently-shaped wells are shown which are useful in the present invention.

The sets of complementary wells 68, 70, 72 and 74 do not require ridges in the strips 76, 78, 80 and 82 which complement slots in the plate 10 as explained above, since the outer diameter of the tubular member 44 in these wells is less than the width of the smaller portion of these wells. The tubular member 44 in wells 84 and 88 do not have areas with a diameter smaller than the outside diameter of the tubular member 44. Therefore, ridges 50 in the strips 90 and 92 are provided to maintain the member 44 in a portion of the wells 84 and 88 when a pipette is not inserted. Thus the means for retaining the tubular members 44 within a given portion of the wells in plate 10 can comprise a complementary set of ridges and slots or, preferably, shaping the wells to have a portion of the wells with a diameter smaller than the outer diameter of the tubular members 44 on 47.

Referring to FIGS. 12 and 13, the well shape for retaining the tubular member 47 can comprise an extension 94 extending from wall 96 of well 98. The distance between the end 99 of extension 94 and the opposing portion of wall 96 in less than the outer diameter of tubular member 47 so that tubular member 47 cannot by-pass extension 94.

Referring to FIGS. 14 and 15, the well shape for retaining the tubular member 47 comprises an extension extending from the floor 93 of well 95. The distance between the extension 91 and the wall 97 is less than the outer diameter of tubular member 47 so that the tubular member 47 is retained within the area shown.

I claim:

1. A test plate having at least one set of wells, each of said set of well comprising two essentially parallel rows of wells, each of said wells comprising a first volume containing a separate enclosure having a membrane means for effecting a fluid interaction process and means for maintaining said separate enclosure within the first volume, and a second volume having a dimension smaller than an outside dimension of said separate enclosure to prevent said separate enclosure from entering said second volume, said second volume having a shape which permits introduction of means for adding or removing liquid from said second volume.

2. The test plate of claim 1 wherein said wells have a tear drop comprising a circular portion cross section for said second volume formed from two converging legs.

3. The test plate of claim 2 wherein a first well from a first row in each set has a first leg positioned essentially parallel to a second leg of a second well in a second row along substantially the entire length of said first leg and said second leg within a central area between said parallel rows.

4. The test plate of claim 1 wherein said wells are L-shaped having a base section and a leg section wherein said leg sections extend into a central area between said parallel rows.

5. The test plate of claim 1 including an extension means extending from a wall of each of said wells to prevent said housing means from entering said second volume.

6. The test plate of claim 1 including a ion means extending from a floor of each of said wells to prevent said housing means from entering said second volume.

7. The test plate of any one of claims 1, 2, 3 or 4, wherein said separate enclosure comprises a hollow tubular member positioned within each well of said test plate, said tubular member having an open end and a closed end covered by the membrane means.

8. The test plate of any one of claims 1, 2, 3 or 4, wherein said separate enclosure comprises a plurality of hollow tubular members each positioned within a well of said test plate, said tubular members within a row of said test plate being molded integrally, each of said tubular members having an open end and closed end covered by the membrane means.

9. The test plate of any one of claim 1, 2, 3 or 4, wherein said separate enclosure comprises a plurality of hollow tubular members each positioned within a well of said test plate, a set of tubular members being formed integrally for positioning within adjacent wells of the adjacent rows of wells, each of said tubular members having an open end and a closed end covered by the membrane means said means for maintaining said tubular members within the first volumes of said wells being positioned in adjacent rows of wells.

* * * * *

UNITED STATES PATENT AND TRADEMARK OFFICE
CERTIFICATE OF CORRECTION

PATENT NO. : 5,141,718
DATED : August 25, 1992
INVENTOR(S) : Phillip Clark

It is certified that error appears in the above-indentified patent and that said Letters Patent is hereby corrected as shown below:

Column 5, Claim 6, line 3, replace "a ion" with --an extension--.

Column 4, line 55, after "drop" --insert --shape--.

Signed and Sealed this

Nineteenth Day of October, 1993

Attest:

BRUCE LEHMAN

*Attesting Officer*  *Commissioner of Patents and Trademarks*